United States Patent [19]

Nakagawa et al.

[11] Patent Number: 5,393,869
[45] Date of Patent: Feb. 28, 1995

[54] PARATHYROID HORMONE DERIVATIVES

[75] Inventors: Shizue Nakagawa, Osaka; Tsunehiko Fukuda, Kyoto; Masahiro Kawase, Kawanishi; Iwao Yamazaki, Takarazuka, all of Japan

[73] Assignee: Takeda Chemical Industries, Ltd., Osaka, Japan

[21] Appl. No.: 765,373

[22] Filed: Sep. 25, 1991

[30] Foreign Application Priority Data

Sep. 28, 1990 [JP] Japan ................................ 2-257490
Sep. 6, 1991 [JP] Japan ................................ 3-227232

[51] Int. Cl.$^6$ .................... A61K 37/00; A61K 37/02; C07K 5/00; C07K 7/00
[52] U.S. Cl. .................................................. 530/324
[58] Field of Search ............................. 530/324; 514/12

[56] References Cited

U.S. PATENT DOCUMENTS 4,423,037 12/1983 Rosenblatt et al. .

FOREIGN PATENT DOCUMENTS

| 0293158 | 11/1988 | European Pat. Off. . |
| 0293159A2 | 11/1988 | European Pat. Off. . |
| 0341963 | 5/1989 | European Pat. Off. ....... C07K 7/10 |
| 0341963 | 11/1989 | European Pat. Off. . |
| 3428942A1 | 2/1985 | Germany . |
| 58-96052 | 6/1983 | Japan . |

OTHER PUBLICATIONS

Coltrera et al., Biochemistry, vol. 19, pp. 4380–4385, 1980.

Rosenblatt et al, Biochemistry, vol. 20, pp. 7246–7250, 1981.

*Primary Examiner*—Lester L. Lee
*Assistant Examiner*—A. M. Davenport
*Attorney, Agent, or Firm*—David G. Conlin; Peter F. Corless

[57] ABSTRACT

Disclosed are peptides and salts thereof represented by general formul $R_1$—Val—Ser—Glu—Ile—Gln—Leu—$R_2$—His—Asn—$R_3$—$R_4$—

$R_5$—His—Leu—Asn—Ser—$R_6$—$R_7$—Arg—$R_8$—Glu—$R_9$—Leu—

$R_{10}$—$R_{11}$—$R_{12}$—Leu—Gln—Asp—Val—His—Asn—$R_{13}$ wherein $R_1$ represents Ser or Aib; $R_2$ represents Met or a naturally occurring hydrophobic amino acid; $R_3$ represents Leu, Ser, Lys or an aromatic amino acid; $R_4$ represents Gly or a D-α-amino acid; $R_5$ represents Lys or Leu; $R_6$ represents Met or a naturally occurring hydrophobic amino acid; $R_7$ represents Glu or a basic amino acid; $R_8$ represents Val or basic amino acid; $R_9$ represents Trp or 2-(1,3-dithiolane-2-yl)Trp; $R_{10}$ represents Arg or His; $R_{11}$ represents Lys or His; $R_{12}$ represents Lys, Gln or Leu; and $R_{13}$ represents Phe or Phe-NH$_2$; except that simultaneously $R_1$ consists of Ser, $R_2$ consists of Met, $R_3$ consists of Leu, $R_4$ consists of Gly, D-Ala or D-Pro, $R_5$ consists of Lys, $R_6$ consists of Met, $R_7$ consists of Glu, $R_8$ consists of Val, $R_9$ consists of Trp, $R_{10}$ consists of Arg, $R_{11}$ consists of Lys and $R_{12}$ consists of Lys.

The parathyroid hormone (1–34) analogs are useful in hormone therapy.

12 Claims, No Drawings

PARATHYROID HORMONE DERIVATIVES

BACKGROUND OF THE INVENTION

The present invention relates to novel parathyroid hormone peptide derivatives useful in hormone therapy.

Parathyroid hormone (PTH) is synthesized in the parathyroid, and plays an important role in controlling blood calcium concentrations or phosphoric acid ion concentrations by acting on the bone, the kidney and the intestine which are its target organs. PTH is a peptide hormone consisting of 84 amino acids, and the biological action thereof can be reproduced by a peptide fragment of an N-terminal (1 through 34 amino acid) portion, G. W. Tregear et al., *Endocrinology* 93, 1349-1353 (1973).

The amino acid sequence of the peptide fragment of the N-terminal (1 through 34 amino acid) portion of this human type PTH (this peptide fragment is hereinafter abbreviated as human PTH(1-34) or hPTH(1-34)) is as follows:

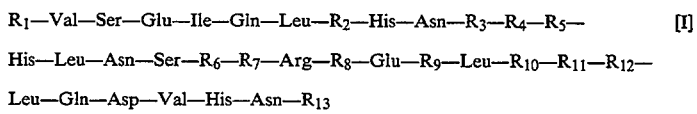
(SEQ ID NO: 1)

```
 1    2    3    4    5    6    7    8    9    10   11   12   13
H—Ser—Val—Ser—Glu—Ile—Gln—Leu—Met—His—Asn—Leu—Gly—Lys—

14   15   16   17   18   19   20   21   22   23   24   25   26
His—Leu—Asn—Ser—Met—Glu—Arg—Val—Glu—Trp—Leu—Arg—Lys—

27   28   29   30   31   32   33   34
Lys—Leu—Gln—Asp—Val—His—Asn—Phe—OH
```

From the biological action of PTH, it is expected that the use of PTH as a drug will provide a drug useful for various bone diseases and the like. However, the following properties of the peptide make it difficult:

(1) The peptide is easily decomposed by various enzymes within the body;
(2) The absorption efficiency of the peptide into the body through various routes is very low; and
(3) The peptide is unstable to various physicochemical conditions such as oxidation.

In order to solve such problems and to understand the relationship between structure and activity of the above hormone, various derivatives have been synthesized for the PTH(1-34) fragment. While, such syntheses have been conducted for bovine PTH(1-34), few examples are known for the human PTH(1-34). For example in one such derivative, when the C-terminus Phe of the human PTH(1-34) is converted to Phe-NH$_2$, an increase in activity is observed (Japanese Patent Unexamined Publication No. 58-96052). This increase in activity is believed to be due to inhibition of carboxypeptidase which decomposes the hormone. Further, human PTH(1-34) contains two Met residues. A molecule in which these Met residues are substituted with Nle residues prevents the hormone from losing its activity due to oxidation (Japanese Patent Unexamined Publication No. 61-24598).

SUMMARY OF THE INVENTION

In order to solve the above described problems, the inventors substituted one or more amino acid residue of human PTH(1-34) by chemical synthesis. The substitutions effect the resulting molecule's resistance to various proteases, its two-dimensional structure as well as its reaction in hydrophilic/hydrophobic or ionic media. By substituting the amino acid unstable to acidic, basic or oxidation conditions with an amino acid stable to these conditions, a molecule which is an object of the present invention is synthesized. In addition, clinically effective PTH analogues have been synthesized in accordance with the present invention.

Namely, the present invention provides:

(1) a peptide represented by general formula [I] or a salt thereof:

$$R_1—Val—Ser—Glu—Ile—Gln—Leu—R_2—His—Asn—R_3—R_4—R_5—$$
$$His—Leu—Asn—Ser—R_6—R_7—Arg—R_8—Glu—R_9—Leu—R_{10}—R_{11}—R_{12}—$$
$$Leu—Gln—Asp—Val—His—Asn—R_{13}$$ [I]

wherein $R_1$ represents Ser or Aib; $R_2$ represents Met or naturally occuring hydrophobic amino acid; $R_3$ represents Leu, Ser, Lys or an aromatic amino acid; $R_4$ represents Gly or a D-α-amino acid; $R_5$ represents Lys or Leu; $R_6$ represents Met or naturally occurring hydrophobic amino acid; $R_7$ represents Glu or a basic amino acid; $R_8$ represents Val or a basic amino acid; $R_9$ represents Trp or 2-(1,3-dithiolane-2-yl)Trp; $R_{10}$ represents Arg or His; $R_{11}$ represents Lys or His; $R_{12}$ represents Lys, Gln or Leu; and $R_{13}$ represents Phe or Phe-NH$_2$. However, except that simultaniously $R_1$ consists of Ser, $R_2$ consists of Met, $R_3$ consists of Leu, $R_4$ consists of Gly, D-Ala or D-Pro, $R_5$ consists of Lys, $R_6$ consists of Met, $R_7$ consists of Glu, $R_8$ consists of Val, $R_9$ consists of Trp, $R_{10}$ consists of Arg, $R_{11}$ consists of Lys and $R_{12}$ consists of Lys (SEQ ID NO:2).

DESCRIPTION OF THE PREFERRED EMBODIMENTS

Naturally occurring hydrophobic amino acids of $R_2$ and $R_6$ mean hydrophobic ones among amino acids which consist of natural proteins originating from animal, plant or microorganisms, and including Leu, Ile, Val, Phe and Trp. Aromatic amino acids of $R_3$ include Phe, β-naphthyl Ala, Trp and Tyr. D-α-amino acids of $R_4$ may be any D-α-amino acid, and includes D-Leu, D-Ile, D-Nle, D-Val, D-Ser, D-Ser(But), D-Abu, D-Thr, D-Nva, D-Met, D-B-naphthyl-Ala, D-Trp, D-Tyr, D-Lys, D-Lys(Fmoc), D-Phe and D-Asn. Generally, neutral amino acids are preferable including D-Ser, D-Leu, D-naphthyl Ala, D-Trp, D-Asn and D-Tyr. Basic amino acids of $R_7$ and $R_8$ include Arg, Lys, Asn and His. The substitution of the above-described groups may be at one or more positions and the substitution combination up to three positions is preferable. Accordingly, a peptide or a salt thereof of the formula [1] may simultaneously have 10 to 12 amino acids optionally selected from a group consisting of Ser for $R_1$, Met for $R_2$, Leu for $R_3$, Gly for $R_4$, Lys for $R_5$, Met for $R_6$, Glu for $R_7$, Val for $R_8$, Trp for $R_9$, Arg for $R_{10}$, Lys for $R_{11}$, Lys for $R_{12}$ and Phe for $R_{13}$.

Peptide synthesis in the present invention can be carried out by the use of an automatic peptide synthesizer. The method of R. B. Merrifield *Advances in Enzymology* 32, 221–296 (1969) applies correspondingly to a basic synthesis course. In this method, the amino acid of the carboxyl terminus is covalently bound to a resin carrier, and elimination of a protective group of an α-amino group and condensation of a protected amino acid are repeated in turn to extend a peptide chain to the amino terminus, thereby obtaining a protected peptide resin having a desired amino acid sequence. This method is based on the above-described principle. The condensation of each amino acid and the elimination of the protective groups of the α-amino groups are performed under approximately similar conditions, and purification of intermediates is not conducted. In synthesizing peptides, therefore, skill of a high order generally is not required. Moreover, the peptides are rapidly synthesized by this method, so that this method is very convenient to synthesize various peptides. The protected peptide resin thus obtained is reacted with, for example, anhydrous hydrogen fluoride, trifluoromethanesulfonic acid or trifluoroacetic acid in the coexistence of various additives, whereby elimination of the peptide from the resin and removal of all protective groups can be achieved in one step.

The resulting crude peptide can be purified by known means for purifying peptides or proteins. Examples of such means include column chromatography under various principles such as gel filtration, ion exchange chromatography using a cation exchange resin or an anion exchange resin, hydrophobic chromatography and partition adsorption chromatography, and high performance liquid chromatography.

The peptides of the present invention can be obtained in various salt forms. Examples of the salts include salts of inorganic acids, salts of organic acids such as formic acid, acetic acid, tartaric acid and citric acid, salts of inorganic bases such as sodium and ammonium, and salts of organic bases such as triethylamine, ethylamine and methylamine.

The human PTH(1–34) derivative peptides represented by general formula [I] of the present invention can be used as therapeutic agents for osteoporosis, hypoparathyroidism and hypertension. The forms thereof include injections, nasotracheal absorption agents, perrectum absorption agents, transvaginal absorption agents, percutaneous absorption agents and eye drops. In some cases, they are orally administered.

When the peptides are used as such therapeutic agents, effective amounts thereof are used to treat mammals, especially humans. Although they are generally used within the range of 1 ng to 100 μg/kg of weight, precise amounts thereof may be determined by those skilled in the art.

When the peptides are used as the therapeutic agents, they must be carefully purified so as to contain no bacteria and no pyrogens.

The peptides, when used as the therapeutic agents for osteoporosis and the like, can be administered parenterally in the form of the above-described injections, nasotracheal absorption agents, perrectum absorption agents, transvaginal absorption agents, percutaneous absorption agents or eye drops, solely or in combination with pharmaceutically acceptable carriers, excipients or diluents. In the case of the injections, it is appropriate that the peptides are given to adults in a dose of 50 ng/kg to 5 mg/kg for 1 to 3 days, and preferably in a dose of 1 to 500 μg/kg for 1 to 3 days. For the injections, it is appropriate that the concentration of the therapeutic agent is 10 to 100 μg/ml.

When nucleotides, amino acids and the like are indicated by abbreviations in this specification, the abbreviations adopted by the IUPAC-IUB Commission on Biochemical Nomenclature or those commonly used in the art are employed. For example, the following abbreviations are used. When the amino acids are capable of existing as optical isomers, it is understood that the L-forms are represented unless otherwise specified.

Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Asparagine
Gln or Q: Glutamine
Aib: Aminoisobutyric acid
Nle: Norleucine
β-Ala: β-Alanine
hPTH: Human PTH
Fmoc: 9-Fluorenylmethoxycarbonyl
Nva: Norvaline
Abu: α-Aminobutyril acid By the amino acid substitution in the PTH(1–34) as described above, the resistance to various proteases is increased and the persistence of the activity in blood is obtained. This is achieved by, for example, substituting Aib for the 1st-position of PTH(1–34), and D-α-amino acid for the 12th-position of PTH(1–34). The position around the 12-position Gly is considered to have the β-turn structure. The substitution of a D-α-amino acid for the Gly, particularly of a bulky D-α-amino acid such as D-Leu, D-Trp or D-Val, contributes to the stabilization of this structure, and the peptide chain is prevented from being digested by a protease at this position. Substitution of naturally occurring hydrophobic amino acid for Met at 8th or 18th position of PTH(1–34) increases resistance to oxidation, and is useful in prevention of reduction or elimination of activity of the peptide. Further, the affinity of the PTH derivatives for receptors is increased and high PTH activity is expressed by the substitution of amino acid residues at other positions. For example, the 11th position of PTH(1–34) is originally Leu. However, it is more preferrable that the amino acid having an aromatic chain such as Phe, is substituted for Leu. Substitution for the 25th, 26th and 27th position basic amino acid of PTH(1–34), especially substitution of Gln or Leu for the 27th Lys; and substitution of 2-(1,3-dithiolane-2-yl)Trp for the 23rd Trp bring about high PTH activity expression. It is understood, that the typical examples of amino acid substitution are not intended to limit the scope of the invention.

Example 1 Synthesis and Purification of PTH (1-34) Active Fragment Analogues

The peptides were synthesized in accordance with a modified method of the solid phase peptide synthesis developed by R. B. Merrifield, R. B. Merrifield, *Adv. Enzymol.* 32, 221-296 (1969), and an automatic peptide synthesizer 430A (Applied Biosystems) was used. Protected peptide-resins were synthesized using protocols specified by Applied Biosystems. Protected amino acid-p-oxymethylphenylacetoamidomethyl resins (polystyrene-1% divinylbenzene) are used as starting materials when analogues having free carboxylic acids as carboxyl termini are desired, and 4-methylbenzhydryl resins are used as starting materials when analogues of carboxylamides are desired, and protected amino acids were condensed thereto successively. In order to protect an α-amino group of each amino acid on condensation, a tertiary-butyloxycarbonyl (BOC) group was used. Side functional groups were protected in the following manner. Hydroxyl groups of serine and threonine were protected as O-benzyl ethers, a hydroxyl group of tyrosine as a p-bromobenzyloxycarbonyl ester, carboxyl groups of glutamic acid and aspartic acid as benzyl esters, imidazole nitrogen of histidine with benzyloxymethyl, a side chain amino group of lysine with 2-chlorobenzyloxycarbonyl, a guanidine functional group of arginine with a p-toluenesulfonyl group, and indoleimine of tryptophan with a formyl group. All amino acids were obtained from Applied Biosystems Japan and Bachem Chemicals.

After all of the amino acids were condensed on the resin, the protected peptide resin was taken out of the synthesizer and dried. The peptide resin (1 g) was allowed to react with anhydrous hydrogen fluoride (8 ml) containing p-cresol (1 ml), 1,2-ethanedithiol (1 ml) and 2-mercaptopyridine (100 mg) at 0° C. for 2 hours. After completion of reaction, hydrogen fluoride was removed by distillation and the residue was washed with diethyl ether to remove most of additives. The peptide was extracted with 3% acetic acid (10 ml), and the resin was removed by filtration. The filtrate was purified by gel filtration using a Sephadex G-25 column. The conditions of gel filtration were as follows: column size: 2.8×60 cm; detecting wavelength: 230 or 280 nm; solvent: 3% acetic acid; flow rate: 40 ml/hour. Fractions containing the peptide were collected and then lyophilized. The resulting powder sample was further purified by reversed phase high performance liquid chromatography [column: YMC-pack, A-324 ODS (10×250 mm); eluting solvent A: 0.1% trifluoroacetic acid-99.9% water; eluting solvent B: 0.1% trifluoroacetic acid-99.9% acetonitrile; linear gradient elution program: 0 minute (90% A+10% B), 30 minutes (60% A+40% B) (if necessary another elution program may be used); elution rate:-1.6 ml/minute; detecting wavelength: 230 or 280 nm]. Peak fractions containing the desired pure product were collected, and passed through a Bio RAD AGIX8 column (acetate form, 1.8×5 cm). The eluate was combined with the washings, and acetonitrile was removed therefrom by distillation, followed by lyophilization. The peptides thus obtained, the result of amino acids analysis and the retention times on HPLC are shown in Table 1.

In Table 1, a and b are as follows:

a: The peptides were hydrolyzed in a tube sealed with 6N hydrochloric acid under reduced pressure, in the presence of 4% thioglycolic acid at 110° C. for 24 hours, and then subjected to amino acid analysis. Theoretical values are designated in parentheses.

b: Names of compounds (no $NH_2$ at the terminus means COOH):

(1) $(Leu^{18})hPTH(1-34)$
(2) $(Aib^1)hPTH(1-34)$
(3) $(Phe^{11})hPTH(1-34)$
(4) $(D-Trp^{12})hPTH(1-34)$
(5) $(Leu^8)hPTH(1-34)NH_2$
(6) $(D-Tyr^{12})hPTH(1-34)NH_2$
(7) $(D-Ser^{12})hPTH(1-34)NH_2$
(8) $(D-Leu^{12})hPTH(1-34)NH_2$
(9) $(3-(2-naphthyl)-D-Ala^{12})hPTH(1-34)NH_2$
(10) $(Ser^{11})hPTH(1-34)NH_2$
(11) $(Phe^{11},Leu^{18})hPTH(1-34)NH_2$
(12) $(Leu^8, Phe^{11},Leu^{18})hPTH(1-34)NH_2$
(13) $(Lys^{11})hPTH(1-34)NH_2$
(14) $(Phe^{11})hPTH(1-34)NH_2$
(15) $(Arg^{19,21})hPTH(1-34)NH_2$
(16) $(3-(2-naphthyl)-Ala^{11})hPTH(1-34(NH_2)$
(17) $(His^{26})hPTH(1-34(NH_2)$
(18) $(His^{25})hPTH(1-34)$
(19) $(Gln^{27})hPTH(1-34)$
(20) $(Arg^{19,21},2-(1,3-dithiolan-2-yl)-Trp^{23})hPTH(1-34)NH_2$
(21) $(Leu^{27})hPTH(1-34)$
(22) $(Lys^{11})hPTH(1-34)$ c: Retention time of the peptides by high performance liquid chromatography. Analysis conditions: VISTA 5000 high performance liquid chromatography (Varian) linked to 712W autosampler (Waters) was used. Column: YMC-303 ODS (4.6×250 mm); Eluent: A, 0.1% trifluoroacetic acid-99.9% water; B, 0.1% trifluoroacetic acid-99.9% acetonitrile; Eluent concentration gradient program: 0 minute(80% A+20% B), 30 minutes(50% A+50% B); Flow rate 0.7 ml/minute; detective wave length 280 nm.

TABLE 1-1

| Amino acid composition of PTH(1-34)analogues(a) | | | | | | |
|---|---|---|---|---|---|---|
| | peptide (b) | | | | | |
| amino acid | (1) | (2) | (3) | (4) | (5) | (6) |
| Asx | 4.00(4) | 4.00(4) | 4.00(4) | 4.00(4) | 4.00(4) | 4.00(4) |
| Ser | 2.44(3) | 1.57(2) | 2.23(3) | 2.45(3) | 2.36(3) | 2.48(3) |
| Glx | 5.28(5) | 5.30(5) | 4.99(5) | 5.22(5) | 5.24(5) | 5.30(5) |
| Gly | 1.03(1) | 1.02(1) | 1.04(1) | | 1.02(1) | |
| Val | 2.37(3) | 2.77(3) | 2.75(3) | 2.87(3) | 2.61(3) | 2.79(3) |
| Met | 0.98(1) | 1.91(2) | 1.91(2) | 1.91(2) | 0.93(1) | 1.83(2) |
| Ile | 0.92(1) | 0.92(1) | 0.89(1) | 1.00(1) | 0.88(1) | 0.95(1) |
| Leu | 6.53(6) | 5.03(5) | 4.07(4) | 5.07(5) | 6.19(6) | 5.10(5) |
| Phe | 1.01(1) | 1.01(1) | 2.02(2) | 1.05(1) | 1.03(1) | 1.02(1) |
| Lys | 3.09(3) | 3.04(3) | 3.03(3) | 2.94(3) | 3.07(3) | 3.05(3) |
| His | 2.80(3) | 2.88(3) | 2.86(3) | 2.80(3) | 2.80(3) | 2.81(3) |
| Trp | 0.90(1) | 1.09(1) | 1.06(1) | 1.90(2) | 0.96(1) | 0.92(1) |
| Arg | 2.00(2) | 1.97(2) | 1.98(2) | 1.99(2) | 2.02(2) | 1.96(2) |
| Aib | | 1.04(1) | | | | |
| Tyr | | | | | | 1.02(1) |
| HPLC retention time (minutes) c | 24.2 | — | — | — | 24.6 | 24.0 |

TABLE 1-2

Amino acid composition of PTH(I-34)analogues(a)

| amino acid | peptide (b) | | | | |
|---|---|---|---|---|---|
| | (7) | (8) | (9) | (10) | (11) |
| Asx | 4.00(4) | 4.00(4) | 4.00(4) | 4.00(4) | 4.00(4) |
| Ser | 3.39(4) | 2.35(2) | 2.45(3) | 3.29(4) | 2.07(3) |
| Glx | 5.17(5) | 5.08(5) | 5.31(5) | 5.14(5) | 4.80(5) |
| Gly | | | | 1.03(1) | 0.83(1) |
| Val | 2.83(3) | 2.73(3) | 2.58(3) | 2.55(3) | 2.43(3) |
| Met | 1.90(2) | 1.90(2) | 2.11(2) | 2.10(2) | 1.03(1) |
| Ile | 0.94(1) | 0.85(1) | 0.90(1) | 0.91(1) | 0.92(1) |
| Leu | 5.04(5) | 5.97(6) | 4.98(5) | 3.92(4) | 4.69(5) |
| Phe | 1.05(1) | 1.00(1) | 1.07(1) | 1.06(1) | 1.70(2) |
| Lys | 2.98(3) | 2.93(3) | 2.81(3) | 2.81(3) | 2.57(3) |
| His | 2.78(3) | 2.81(3) | 2.67(3) | 2.66(3) | 2.30(3) |
| Trp | 1.06(1) | 0.86(1) | 0.89(1) | 0.70(1) | 0.90(1) |
| Arg | 2.01(2) | 1.96(2) | 1.88(2) | 1.79(2) | 1.61(2) |
| Aib | | | | | |
| Tyr | | | | | |
| HPLC retention time (minutes) c | 21.9 | 26.4 | 28.1 | 20.8 | 27.1 |

TABLE 1-3

Amino acid composition of PTH(1-34)analogues(a)

| amino acid | peptide (b) | | | | | |
|---|---|---|---|---|---|---|
| | (12) | (13) | (14) | (15) | (16) | (17) |
| Asx | 4.00(4) | 4.00(4) | 4.00(4) | 4.00(4) | 4.00(4) | 4.00(4) |
| Ser | 2.07(3) | 1.99(2) | 2.51(3) | 2.55(3) | 2.55(3) | 2.58(3) |
| Glx | 4.83(5) | 4.71(5) | 4.94(5) | 3.95(4) | 4.98(5) | 5.05(5) |
| Gly | 1.01(1) | 0.96(1) | 1.01(1) | 1.02(1) | 1.03(1) | 1.04(1) |
| Val | 2.65(3) | 2.63(3) | 2.73(3) | 1.80(2) | 2.73(3) | 2.75(3) |
| Met | | 1.66(2) | 2.12(2) | 2.12(2) | 1.90(2) | 1.91(2) |
| Ile | 0.81(1) | 0.67(1) | 0.84(1) | 0.86(1) | 0.86(1) | 0.91(1) |
| Leu | 5.97(6) | 3.92(4) | 4.08(4) | 5.08(5) | 4.07(4) | 5.08(5) |
| Phe | 1.99(2) | 1.06(1) | 2.04(2) | 1.04(1) | 1.03(1) | 1.00(1) |
| Lys | 2.92(3) | 3.76(4) | 2.96(3) | 2.88(3) | 3.03(3) | 2.00(2) |
| His | 2.53(3) | 2.45(3) | 2.69(3) | 2.68(3) | 3.09(3) | 4.07(4) |
| Trp | 0.65(1) | 0.79(1) | 0.87(1) | 0.86(1) | 0.92(1) | 0.91(1) |
| Arg | 1.93(2) | 2.21(2) | 1.94(2) | 3.84(4) | 1.96(2) | 1.91(2) |
| Aib | | | | | | |
| Tyr | | | | | | |
| HPLC retention time (minutes) c | 28.4 | 20.8 | 28.1 | 26.6 | 24.8 | 23.4 |

TABLE 1-4

Amino acid composition of PTH(1-34)analogues(a)

| amino acid | peptide (b) | | | | |
|---|---|---|---|---|---|
| | (18) | (19) | (20) | (21) | (22) |
| Asx | 4.00(4) | 4.00(4) | 4.00(4) | 4.00(4) | 4.00(4) |
| Ser | 2.58(3) | 2.72(3) | 2.51(3) | 2.99(3) | 2.49(3) |
| Glx | 5.07(5) | 6.27(6) | 3.92(4) | 4.90(5) | 5.04(5) |
| Gly | 1.04(1) | 1.00(1) | 0.99(1) | 1.31(1) | 1.08(1) |
| Val | 2.76(3) | 2.76(3) | 1.78(2) | 2.77(3) | 2.78(3) |
| Met | 1.91(2) | 1.91(2) | 2.03(2) | 1.82(2) | 2.12(2) |
| Ile | 0.89(1) | 0.90(1) | 0.87(1) | 0.91(1) | 0.91(1) |
| Leu | 5.11(5) | 5.05(5) | 5.04(5) | 5.90(6) | 3.96(4) |
| Phe | 1.02(1) | 0.96(1) | 1.04(1) | 1.00(1) | 1.01(1) |
| Lys | 3.02(3) | 1.91(2) | 2.79(3) | 1.87(2) | 3.86(3) |
| His | 3.64(4) | 2.66(3) | 2.64(3) | 2.79(3) | 2.74(3) |
| Trp | 0.95(1) | 0.84(1) | 0.84(1) | 0.79(1) | 0.85(1) |
| Arg | 0.98(1) | 1.86(2) | 3.83(4) | 1.91(2) | 1.90(2) |
| Aib | | | | | |
| Tyr | | | | | |
| HPLC retention time (minutes) c | 24.8 | 26.0 | 28.2 | 29.2 | 23.6 |

Example 2 Synthesis and Purification of (Arg$^{19,21}$,2-(1,3-dithiolane-2-yl)Trp$^{23}$)hPTH(1–34)NH$_2$ 560 mg of peptide resin synthesizing (Arg$^{19,21}$)hPTH(1–34)NH$_2$ was allowed to react with anhydrous hydrogen fluoride (5 ml) containing p-cresol (620 μl) and ethanedithiol(620 μl) at 0° C. for 2 hours. After hydrogen fluoride was removed by distillation, the residue was washed with diethyl ether containing 0.1% 2-mercaptoethanol. The resulting product was dried and the peptide was extracted with trifluoroacetic acid (5 ml), and the resin was removed by filtration. Ether was added to the filtrate and the resulting precipitate was separated by filtration and washed with ether. 280 mg of the crude peptide was obtained. The peptide was purified by reverse phase high performance liquid chromatography. The conditions of the chromatography were as follows: Column, YMC-pack, A-324 ODS (10×250 mm); Eluent A, 0.1% trifluoroacetic acid—99.9% water; Eluent B, 0.1% trifluoroacetic acid—99.9% acetonitrile; Eluent concentration gradient program, 0 minute (70% A+30% B), 40 minutes (55% A +45% B); flow rate: 1.6 ml/minute. Two large peaks (retention times 17.0 minutes and 18.2 minutes) were observed in the chromatography. The former peak (retention time 17.0 minutes) was recovered and changed to acetate by an ion-exchange resin. The acetate was then lyophilized to obtain 4.9 mg of (Arg$^{19,21}$)hPTH(1–34NH$_2$. After hydrolysis, the resulting product shows the correct amino acid composition in the amino acid analysis. The ultraviolet absorption of the product shows a specific curve characteristic of a peptide comprising tryptophan.

6.9 mg of compound was obtained from the latter peak. Amino acid analysis of the compound after acid-hydrolysis showed the correct composition, but amino acid analysis after trypsin-amino peptidase M digestion showed only 0.28 residue of tryptophan and the glutamic acid was detected 0.65 residue less than the theoretical value. Ultraviolet absorption curve for the digested compound showed a peak of 289 nm and a valley of 255 nm. As a result, tryptophan side chain of the compound is deduced to be modified. The following process showed that 1,3-dithiolan linked to the C2 carbon of the side chain indole of tryptophan.

A compound (4mg) obtained from the peak at a retention time 18.2 minutes in the above high performance liquid chromatography was dissolved into 60 mM sodium hydrogen carbonate pH8.0(2.6ml). TPCK-tris-pin(160 μg)was added to the solution and reacted for 24 hours at 37° C., and then was inactivated by heating for 6 minutes at 100° C. Aminopeptidese-M (0.5 mg) was added to the resulting solution adjusted to pH7 and incubated at 37° C. for 24 hours and then the enzyme(0.5 mg) was further added thereto. After an additional 48 hour period, the buffer (10 ml) and the enzyme (1 mg) were added thereto and reacted for 70 hours. The resulting product was subjected to reverse phase high performance liquid chromatography to isolate a modified triptophan. Column, YMC D-ODS-5 S5 120A (20×250m); the same eluent; Eluent program, 0 minute (80%A+20%B), 40 minutes (65%A+35%B); Flow rate, 5 ml/minute; detected at 280 nm. The isolated compound showed a maximum ultraviolet absorption at 289nm. Amino acid analysis after hydrolysis with 6N HCl containing 4% thioglycolic acid showed triptophan. When the product was subjected to high resolution FAB-mass spectrum (Nihon Denshi, Japan; AX-505W TYPE double convergence mass spectrometer), a peak at 309.0734(M+H+) as observed and a molecular formula $C_{14}H_{17}N_2O_2 S_2$ was deduced. Further about 30 ng of the compound was subjected to 1H-MNR(Nihon Denshin, JNM-GX400).

(DMSO-d$_6$), α-CH δ=4.06 (1H, dd like), β-CH$_2$ 3.54(1H, dd), 3.30(1H, dd); 1-NH 10.88 (1H); 5-CH 7.50

(1H, d); 6-CH 7.30 (1H, t like); 7-CH 7.20 (1H, t like); 8-CH 7.68 (1H, d); dithiolan 2CH 6.14 (1H, S); dithiolan 4CH$_2$ and 5CH$_2$ 3.64 (2H, m) and 3.49 (2H, m).

The above data show that the isolated hPTH(1–34)NH$_2$ analogue has 2-(1,3-dithiolan-2-yl)-tryptophan at 23th position.

Example 3 Assay of Biological Activity of PTH (1–34) Analogues

The biological activity of the peptide analogues was evaluated by a modified version of the method reported by Shigeno et al. in *The Journal of Biological Chemistry* 263, 18369–18377 (1988). A culture solution (Hank's solution, containing 20 mM N-2-hydroxyethylpiperazine-N'-2-ethanesulfonic acid (HEPES), 0.1% bovine serum albumin and 0.5 mM isobutylmethyl-xanthine) containing 0.01, 0.1, 1, 10 or 100 nM analogue was added in an amount of 100 μto a mouse cranial bone-derived osteoblast-like cell strain, MC3T3-EI cells, cultivated on a 96-well multiplate (Nunclon, Nunc), followed by reaction at room temperature for 30 minutes. After addition of 100 μof 0.2N hydrochloric acid, the mixture was immersed in boiling water for 2.5 minutes, and cyclic adenosine monophosphate (cAMP) produced by a PTH receptor was extracted from the cells. The total cAMP in the culture solution and the cells was assayed using a commercial radioimmunoassay kit (cyclic AMP [$^{125}$I] kit "Du Pont-Daiichi", Daiichi Kagaku Yakuhin). An increase in cAMP production depending on the concentration of the human PTH (1–34) added as a standard was observed in each case. The biological activity of the PTH (1–34) peptide analogues is shown in Table 2.

TABLE 2

Biological Activity of PTH(1-34) Partial Peptides (Represented by Relative Activity to hPTH(1-34))

| Peptide | Relative Activity |
|---|---|
| hPTH (1-34) | 1.00 |
| [Leu$^{18}$] hPTH (1-34) | 0.4 |
| [Aib$^1$] hPTH (1-34) | 1.7 |
| [Phe$^{11}$] hPTH (1-34) | 1.1 |
| [Leu$^8$] hPTH (1-34)NH$_2$ | 0.5 |
| [D-Ser$^{12}$] hPTH (1-34)NH$_2$ | 0.8 |
| [D-Leu$^{12}$] hPTH (1-34)NH$_2$ | 0.5 |
| [3-(2-naphthyl)-D-Ala$^{12}$] hPTH (1-34)NH$_2$ | 0.9 |
| [Ser$^{11}$] hPTH (1-34)NH$_2$ | 0.8 |
| [Leu$^8$, Phe$^{11}$, Leu$^{18}$] hPTH (1-34)NH$_2$ | 0.9 |
| [Lys$^{11}$] hPTH (1-34)NH$_2$ | 1.1 |
| [Phe$^{11}$] hPTH (1-34)NH$_2$ | 1.3 |
| [Arg$^{13, 21}$] hPTH (1-34)NH$_2$ | 0.9 |
| [3-(2-naphthyl)-Ala$^{11}$] hPTH (1-34)NH$_2$ | 1.7 |
| [His$^{26}$] hPTH (1-34)NH$_2$ | 0.9 |
| [His$^{25}$] hPTH (1-34) | 1.0 |
| [Gln$^{27}$] hPTH (1-34) | 2.5 |
| [Arg$^{19, 21}$, 2-(1,3-ditiolan-2-yl)-Trp$^{23}$] hPTH (1-34)NH$_2$ | 1.7 |
| [Leu$^{27}$] hPTH (1-34) | 1.2 |

We claim:

1. (twice amended) A peptide or salts thereof having the formula

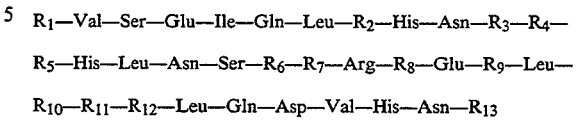

R$_1$—Val—Ser—Glu—Ile—Gln—Leu—R$_2$—His—Asn—R$_3$—R$_4$—

R$_5$—His—Leu—Asn—Ser—R$_6$—R$_7$—Arg—R$_8$—Glu—R$_9$—Leu—

R$_{10}$—R$_{11}$—R$_{12}$—Leu—Gln—Asp—Val—His—Asn—R$_{13}$ wherein R$_1$ represents Ser or Aib; R$_2$ represents Met or a naturally occurring hydrophobic amino acid; R$_3$ represents Leu, Ser, Lys or an aromatic amino acid; R$_4$ represents Gly or a D-α-amino acid; R$_5$ represents Lys or Leu; R$_6$ represents Met or a naturally occurring hydrophobic amino acid; R$_7$ represents Glu or a basic amino acid; R$_8$ represents Val or a basic amino acid; R$_9$ represents Trp or 2-(1,3-dithiolane-2-yl)Trp; R$_{10}$ represents Arg or His; R$_{11}$ represents Lys or His; R$_{12}$ represents Lys, Gln or Leu; and R$_{13}$ represents Phe or Phe-NH$_2$;

with the exclusion of:

(1) the peptide or salt thereof wherein R$_1$ is Ser, R$_2$ is Met, R$_3$ is Leu, R$_4$ is Gly, R$_5$ is Lys, R$_6$ is Met, R$_7$ is Glu, R$_8$ is Val, R$_9$ is Trp, R$_{10}$ is Arg, R$_{11}$ is Lys and R$_{12}$ is Lys;

(2) the peptide or salt thereof wherein R$_1$ is Ser, R$_2$ is Met, R$_3$ is Leu, R$_4$ is D-Ala, R$_5$ is Lys, R$_6$ is Met, R$_7$ is GlU, R$_8$ is Val, R$_9$ is Trp, R$_{10}$ is Arg, R$_{11}$ is Lys and R$_{12}$ is Lys; and (3) the peptide or salt thereof wherein R$_1$ is Ser, R$_2$ is Met. R$_4$ is D-Pro, R$_5$ is Lys, R$_6$ is Met, R$_7$ is Glu, R$_8$ is Val, R$_9$ is Trp, R$_{10}$ is Arg, R$_{11}$ is Lys and R$_{12}$ is Lys.

2. The peptide of claim 1 wherein a naturally occurring hydrophobic amino acid in R$_2$ and R$_6$ is Leu, Ile, Val, Phe or Trp.

3. The peptide of claim 1 wherein an aromatic amino acid in R$_3$ is Phe, β-naphthyl Ala, Trp or Tyr.

4. The peptide of claim 1 wherein a D-α-amino acid is D-Leu, D-Ile, D-Nle, D-Val, D,Ser, D-Ser(But), D-Abu, D-Thr, D-Nva, D-Met, D-naphthyl-D-Ala, D-Trp, D-Tyr, D-Lys, D-Lys(Fmoc), D-Phe or D-Asn.

5. The peptide of claim 1 wherein a D-α-amino acid is a neutral amino acid.

6. The peptide of claim 5 wherein neutral D-α-amino acid is D-Ser, D-Leu, D-naphthyl Ala, D-Trp, D-Asn or D-Tyr. Tyr.

7. The peptide of claim 1 wherein basic amino acid in R$_7$ and R$_8$ is Arg, Lys, Asn or His.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 34 amino acids
( B ) TYPE: amino acid
( D ) TOPOLOGY: linear (ii) MOLECULE TYPE: peptide (v) FRAGMENT TYPE: N-terminal (xi) SEQUENCE DESCRIPTION: SEQ ID NO:1:

```
Ser Val Ser Glu Ile Gln Leu Met His Asn Leu Gly Lys His Leu Asn
1               5                   10                  15
Ser Met Glu Arg Val Glu Trp Leu Arg Lys Lys Leu Gln Asp Val His
                20                  25                  30
Asn Phe
```

(2) INFORMATION FOR SEQ ID NO:2:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa=Ser or Aib"

(ix) FEATURE:
        (A) NAME/KEY: Modified-site
        (B) LOCATION: 8
        (D) OTHER INFORMATION: /note="Xaa=Met or naturally
            occurring hydrophobic amino acid"

(ix) FEATURE:
        (A) NAME/KEY: Modified-site
        (B) LOCATION: 11
        (D) OTHER INFORMATION: /note="Xaa=Leu, Ser, Lys or
            aromatic amino acid"

(ix) FEATURE:
        (A) NAME/KEY: Modified-site
        (B) LOCATION: 12
        (D) OTHER INFORMATION: /note="Xaa=Gly or D-amino acid"

(ix) FEATURE:
        (A) NAME/KEY: Modified-site
        (B) LOCATION: 13
        (D) OTHER INFORMATION: /note="Xaa=Lys or Leu"

(ix) FEATURE:
        (A) NAME/KEY: Modified-site
        (B) LOCATION: 18
        (D) OTHER INFORMATION: /note="Xaa=Met or naturally
            occurring hydrophobic amino acid"

(ix) FEATURE:
        (A) NAME/KEY: Modified-site
        (B) LOCATION: 19
        (D) OTHER INFORMATION: /note="Xaa=Glu or basic amino
            acid"

(ix) FEATURE:
        (A) NAME/KEY: Modified-site
        (B) LOCATION: 21
        (D) OTHER INFORMATION: /note="Xaa=Val or basic amino
            acid"

(ix) FEATURE:
        (A) NAME/KEY: Modified-site
        (B) LOCATION: 23
        (D) OTHER INFORMATION: /note="Xaa=Trp or
            2-(1,3- dithionlan-2-yl)Trp"

(ix) FEATURE:
        (A) NAME/KEY: Modified-site
        (B) LOCATION: 25
        (D) OTHER INFORMATION: /note="Xaa=Arg or His"

(ix) FEATURE:
        (A) NAME/KEY: Modified-site (B) LOCATION: 26
        (D) OTHER INFORMATION: /note="Xaa=Lys or His"

(ix) FEATURE:
        (A) NAME/KEY: Modified-site
        (B) LOCATION: 27
        (D) OTHER INFORMATION: /note="Xaa=Lys, Gln or Leu"

(ix) FEATURE:
        (A) NAME/KEY: Modified-site
        (B) LOCATION: 34
        (D) OTHER INFORMATION: /note="Xaa=Phe or Phe-NH2"

(xi) SEQUENCE DESCRIPTION: SEQ ID NO:2:

Xaa Val Ser Glu Ile Gln Leu Xaa His Asn Xaa Xaa Xaa His Leu Asn
 1               5                       10                  15

Ser Xaa Xaa Arg Xaa Glu Xaa Leu Xaa Xaa Xaa Leu Gln Asp Val His
         20                  25                      30

Asn Xaa

8. The peptide of claim 1 wherein the peptide or salts thereof having 10 to 12 amino acids optionally selected from a group consisting of Ser for $R_1$, Met for $R_2$, Leu for $R_3$, Gly for $R_4$, Lys for $R_5$, Met for $R_6$, Glu for $R_7$, Val for $R_8$, Trp for $R_9$, Arg for $R_{10}$, Lys for $R_{11}$, Lys for $R_{12}$ and Phe for $R_{13}$.

9. A peptide or salts thereof selected from the group consisting of $(Leu^{18})hPTH(1-34)$, $(Aib^1)hPTH(1-34)$, $(Phe^{11})hPTH(1-34)$, $(D-Trp^{12})hPTH(1-34)$, $(Leu^8)hPTH(1-34)$ $NH_2$, $(D-Tyr^{12})hPTH(1-34)NH_2$, $(D-Ser^{12})hPTH(1-34)NH_2$, $(D-Leu^{12})hPTH-(1-34)NH_2$, $(3-(2-naphthyl-D-Ala^{12})hPTH(1-34)NH_2$, $(Ser^{11})hPTH(1-34)NH_2$, $(Phe^{11},Leu^{18})hPTH-(1-34)NH_2$, $(Leu^8,Phe^{11},Leu^{18})hPTH(1-34)NH_2$, $(Lys^{11})hPTH(1-34)NH_2$, $(Phe^{11})hPTH(1-34)NH_2$, $(Arg^{19,21})hPTH(1-34)NH_2$, $(3-(2-naphthyl)-Ala^{11})hPTH(1-34)NH_2$, $(His^{26})hPTH(1-34)NH_2$, $(His^{25})hPTH(1-34)$, $(Gln^{27})hPTH(1-34)$, $(Arg^{19,21},2-(1,3-dithiolane-2-yl)Trp^{23})hPTH(1-34)NH_2$, $(Leu^{27})hPTH(1-34)$ and $(Lys^{11})hPTH(1-34)$.

10. The peptide of claim 1 wherein a naturally occurring hydrophobic amino acid in $R_2$ and $R_6$ is Leu, Ile, Val, Phe or Trp; an aromatic amino acid in $R_3$ is Phe, β-naphthyl Ala, Trp or Tyr; and a D-α amino acid is D-Leu, D-Ile, D-Nle, D-Val, D-Ser, D-Ser(But), D-Abu, D-Thr, D-Nva, D-Met, β-naphthyl-D-Ala, D-Trp, D-Tyr, D-Lys, D-Lys(Fmoc), D-Phe or D-Asn.

11. The peptide of claim 1 wherein a naturally occurring hydrophobic amino acid in $R_2$ and $R_6$ is Leu, Ile, Val, Phe or Trp; an aromatic amino acid in $R_3$ is Phe, β-naphthyl Ala, Trp or Tyr; and basic amino acid in $R_7$ and $R_8$ is Arg, Lys, Asn or His.

12. The peptide of claim 11 where a D-α amino acid is D-Leu, D-Ile, D-Nle, D-Val, D-Ser, D-Ser(But), D-Abu, D-Thr, D-Nva, D-Met, β-naphthyl-D-Ala, D-Trp, D-Tyr, D-Lys, D-Lys(Fmoc), D-Phe or D-Asn.

* * * * *

UNITED STATES PATENT AND TRADEMARK OFFICE
CERTIFICATE OF CORRECTION

PATENT NO. : 5,393,869

DATED : February 28, 1995

INVENTOR(S) : Nakagawa et al.

It is certified that error appears in the above-indentified patent and that said Letters Patent is hereby corrected as shown below:

Column 10, line 1 (claim 1), please delete "(twice amended)".

Column 10, line 28 (claim 1), please delete "GlU" and insert --Glu--.

Column 10, line 40 (claim 4), please delete "D,Ser" and insert --D-Ser--.

Column 10, line 41 (claim 4), please delete "D-naphthyl-D-Ala" and insert --β-naphthyl-D-Ala--.

Column 10, line 47 (claim 6), please delete "Tyr. Tyr" and insert --Tyr--.

Signed and Sealed this

Twenty-third Day of July, 1996

Attest:

BRUCE LEHMAN

*Attesting Officer*  *Commissioner of Patents and Trademarks*